US011759401B2

(12) United States Patent
Liu et al.

(10) Patent No.: US 11,759,401 B2
(45) Date of Patent: Sep. 19, 2023

(54) METHOD OF MONITORING MEDICATION REGIMEN WITH PORTABLE APPARATUS

(71) Applicant: Nai-Chia Liu, Taipei (TW)

(72) Inventors: Nai-Chia Liu, Coquitlam (CA); Yu-Pei Chen, Coquitlam (CA)

(73) Assignee: Nai-Chia Liu, Taipei (TW)

( * ) Notice: Subject to any disclaimer, the term of this patent is extended or adjusted under 35 U.S.C. 154(b) by 360 days.

(21) Appl. No.: 17/264,291

(22) PCT Filed: Jul. 30, 2019

(86) PCT No.: PCT/CA2019/000112
§ 371 (c)(1),
(2) Date: Jan. 28, 2021

(87) PCT Pub. No.: WO2020/028967
PCT Pub. Date: Feb. 13, 2020

(65) Prior Publication Data
US 2021/0298994 A1    Sep. 30, 2021

(30) Foreign Application Priority Data
Aug. 8, 2018   (CA) ................................ CA 3013602

(51) Int. Cl.
*A61J 7/04* (2006.01)
*G16H 20/13* (2018.01)
(Continued)

(52) U.S. Cl.
CPC ............. *A61J 7/0481* (2013.01); *A61J 1/035* (2013.01); *A61J 7/0418* (2015.05); *A61J 7/0427* (2015.05);
(Continued)

(58) Field of Classification Search
CPC ...... A61J 7/0481; A61J 1/035; A61J 2205/60; A61J 7/0418; A61J 7/0427; A61J 2205/50; G16H 20/13; G16H 40/67; G16H 80/00
See application file for complete search history.

(56) References Cited

U.S. PATENT DOCUMENTS 9,183,601 B2 * 11/2015 Hanina .................. G16H 10/60
9,679,113 B2 *  6/2017 Hanina .................. G06V 20/52
(Continued)

FOREIGN PATENT DOCUMENTS

CA      2902215 A1    9/2014
JP   2017045372 A    3/2017
(Continued)

OTHER PUBLICATIONS

Search Report dated Apr. 2, 2019 of the corresponding Canadian patent application No. 3,013,602.
(Continued)

*Primary Examiner* — Michael Collins
(74) *Attorney, Agent, or Firm* — Chun-Ming Shih; HDLS IPR SERVICES (57) ABSTRACT

A method of monitoring medication regimen with portable apparatus installed with a blister monitoring software for collecting patient compliance data, including one or multiple blister packages, a unique identification code disposed on each package. An embodiment of the invention includes steps of: logging patient into blister monitoring software with personal credential; capturing image of blister package using portable apparatus; analyzing image of blister package and obtaining unique identification code of package; cross-checking patient identity with package identification code to prevent false medication; automatically recording medication time and remaining tablets or capsules inside blister package. The method of the invention prevents false medi- (Continued)

cation and enables doctors and nurses to remotely track patient's progress in real-time, thus increasing medication compliance.

10 Claims, 8 Drawing Sheets

(51) Int. Cl.
*G16H 40/67* (2018.01)
*A61J 1/03* (2023.01)
*G16H 80/00* (2018.01)

(52) U.S. Cl.
CPC .............. *G16H 20/13* (2018.01); *G16H 40/67* (2018.01); *G16H 80/00* (2018.01); *A61J 2205/50* (2013.01); *A61J 2205/60* (2013.01)

(56) References Cited

U.S. PATENT DOCUMENTS

| | | | | |
|---|---|---|---|---|
| 10,116,903 | B2* | 10/2018 | Hanina | H04N 7/18 |
| 2013/0044196 | A1* | 2/2013 | Guan | G06V 40/16 |
| | | | | 382/128 |
| 2014/0114472 | A1* | 4/2014 | Bossi | G06V 20/66 |
| | | | | 700/240 |
| 2015/0363570 | A1* | 12/2015 | Hanina | G06F 18/00 |
| | | | | 348/143 |
| 2016/0117476 | A1* | 4/2016 | Hanina | G16H 10/60 |
| | | | | 705/3 |
| 2016/0132660 | A1* | 5/2016 | Barajas | G16H 30/40 |
| | | | | 705/2 |
| 2017/0283151 | A1* | 10/2017 | Stormer | G16H 20/10 |
| 2018/0060657 | A1* | 3/2018 | Stuck | G06T 7/70 |

FOREIGN PATENT DOCUMENTS

| | | |
|---|---|---|
| TW | 201638875 A | 11/2016 |
| TW | M564220 U | 7/2018 |
| WO | 2012177524 A1 | 12/2012 |
| WO | 2018156810 A1 | 8/2018 |

OTHER PUBLICATIONS

Office Action dated Sep. 19, 2019 of the corresponding Taiwan patent application No. 107127903.
Search Report dated Nov. 13, 2019 of the corresponding PCT application No. PCT/CA2019/000112.
Office Action dated Mar. 22, 2023 of the corresponding China patent application No. 201810923752.3.

* cited by examiner

METHOD OF MONITORING MEDICATION REGIMEN WITH PORTABLE APPARATUS

CROSS-REFERENCE TO RELATED APPLICATIONS

This application is the National Phase of PCT International Application No. PCT/CA2019/000112 filed on Jul. 30, 2019, which claims priority to CA3,013,602 filed on Aug. 8, 2018. The entire disclosures of the above applications are all incorporated herein by reference.

BACKGROUND OF THE INVENTION

1. Technical Field

This invention relates to monitoring medication regimen in clinical trials and general pharmacy prescriptions by tracking medications in blister packages using portable apparatus having blister monitoring software.

2. Description of Related Art

Present clinical trials and general pharmacy prescriptions have many protocols of medication intake such as requiring patients to take medication before or after meal by swallowing, chewing, or sublingual diffusion under the tongue. The protocols of medication intake are usually taught only once by a pharmacist or a nurse, and can often be difficult for patients to learn, memorize, and record their progress throughout the entire medication regimen.

When a regimen involves multiple medications, a patient must remember the specific appearance and protocol of each medication, and record the time when each medicine is taken. In scheduled clinical appointments, the patient must return all used and unused blister packages, so a pharmacist or a nurse can tally the remaining medications and enter the patient's medication compliance into a computer. This process is time consuming and vulnerable to human errors. Furthermore, pharmacists and nurses are unaware if the patient has forgotten to take medication, took the wrong medication, or took too many or too few medication in between clinical appointments. In the worst-case scenario, the patient may have lost some blister packages which leads to insufficient dosage only to be discovered during a patient's returning appointment. This can lead to delay or failure of the entire clinical trial due to insufficient compliance data. Therefore, current methods of monitoring medication compliance need to be improved.

There are smart pillboxes on the market with a plurality of compartments for storing medications and can record a patient's time of taking medication from a compartment. However, smart pillboxes require the patient to learn a series of operating steps such as unlocking, opening, returning, docking, and connecting wire or wirelessly to a computer. Patients often avert smart pillboxes because they are inconvenient to operate.

Smart pillboxes are also bulky to carry because they are composed of many compartments, mechanical locks, sensors, digital cameras, recorders, wireless transceiver, batteries, etc. Smart pillboxes' bulkiness means patients are unable to record and monitor their medication regimen when travelling outdoors.

Another major drawback of smart pillboxes is that a pharmacist has to open the blister packages sealed by the original manufacturer and redistribute medications into the compartments of the pillbox. Repackaging medications from their original package not only incurs additional personnel cost and the cost of buying the smart pillboxes, it also increases human allocation error and risk of contamination by microbes and pollutants. Furthermore, some medications are sealed in blister packages with nitrogen gas to prevent oxidation, and can start to deteriorate when they are stored in pillboxes. Thus, smart pillboxes are not widely used in clinical trials and improvements are needed.

There are proprietary blister packages on the market with embedded radio-frequency identification (RFID) tags. These packages require embedding RFID tags into the packaging during manufacturing and printing external sensory circuits on the seal of individual blisters. When a patient opens a blister, the sensory circuit is broken and a timestamp is recorded by the RFID. However, this technology is cost prohibitive because existing manufacturing process needs to be modified for embedding RFID and printing circuitry on the package, and proprietary RFID readers are needed to read the information from the RFID tag.

SUMMARY OF THE INVENTION

This invention discloses a method of monitoring medication regimen for patients enrolled in clinical trials and general pharmacy prescription. This method tracks medication in blister packages by using portable apparatus having blister monitoring software, and is aimed to improve patient compliance, carrying mobility, ease of recording medication regimen, reduce personnel cost for hospitals, lower manufacturing cost for pharmaceuticals, and decrease risk of contamination from repackaging medication.

This method of this invention is applied for a portable apparatus installed with a blister monitoring software, and a blister package having a unique identification code disposed thereon and having a plurality of blisters containing tablets or capsules, and the medication monitoring method mainly includes following steps of: a) using the blister monitoring software to display a notification via the portable apparatus on a prescribed medication time; b) obtaining a biometric credential of a patient using the portable apparatus for logging into the blister monitoring software and verifying the patient's identity; c) capturing an image of the blister package using the portable apparatus; d) analyzing the image of the blister package to obtain the unique identification code on the blister package; e) comparing the patient's identity to the unique identification code to determine if the blister package belongs to the patient; f) displaying an alert via the portable apparatus if the blister package is determined not belonging to the patient; and, g) recording a quantity of remaining tablets or capsules inside the blister package and patient's time of taking medication if the blister package is determined belonging to the patient.

This invention enables a pharmacist or nurse to track the medication regimen of a patient in real-time, thus allowing missing dose, under dose and overdose of a patient to be detected promptly. Patients who lost their medication packages can also be detected when they miss consecutive doses.

This invention works with factory-sealed blister packages and uses multiple recognition techniques to rapidly identify remaining tablets or capsules in a package. It requires no pharmacist to repackage medication into specially shaped or color-coded pillbox, and requires no RFID to be embedded into packaging. By largely automating the process of monitoring patient progress and forgo the use of pillbox entirely, this invention improves ease of monitoring medication regimen and carrying mobility, while preserving packaging integrity and reducing personnel costs and contamination risk.

The invention comprising the above steps, the relation of these steps with respect to each other, and the apparatus embodying the features, elements and parts that are adapted to facilitate such steps will be exemplified in the following detailed disclosure with accompanying drawings, and the scope of the invention will be indicated in the claims.

DETAILED DESCRIPTION OF THE INVENTION

This invention is directed to blister packages used in clinical trial and general pharmacy prescription. Specifically, by utilizing the innovations of this invention, a patient may record his or her medicine time and the quantity of the remaining tablets or capsules inside a blister package using a portable apparatus. Therefore, this invention improves a patient's medication compliance, recording convenience, carrying mobility, as well as greatly reducing personnel cost and risk of medication contamination.

Embodiments of the invention will now be described with reference to the accompanying drawings.

Figure 1:
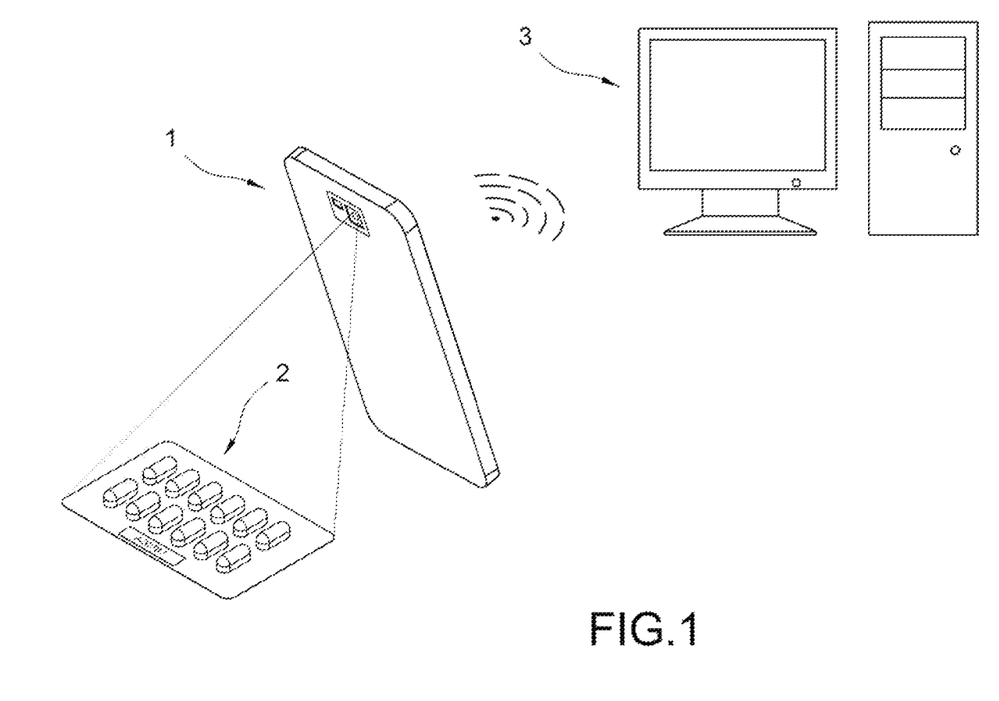
FIG. 1 depicts a medication monitoring method in accordance with a first preferred embodiment of the invention.
Figure 2:
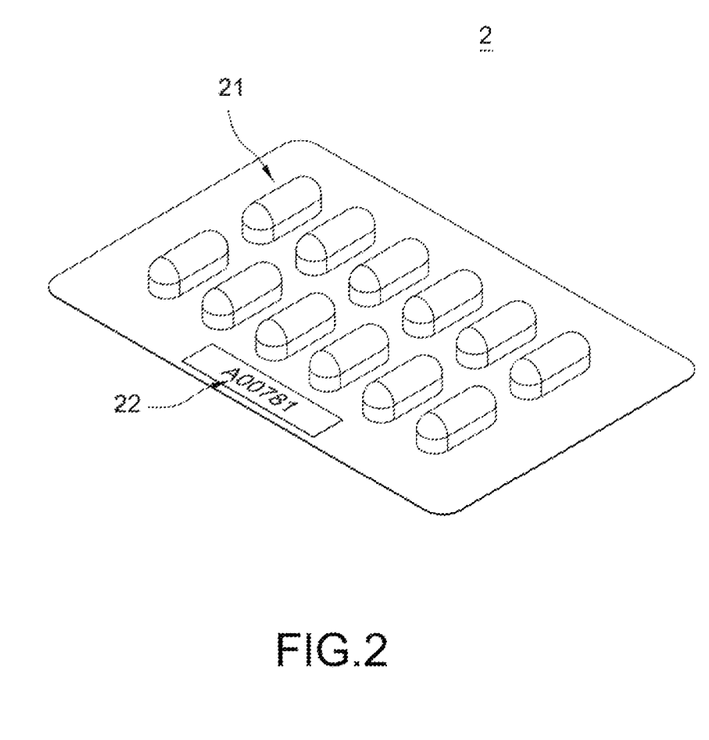
FIG. 2 depicts a perspective view of the blister package shown in FIG. 1.

The invention is directed to a method of monitoring medication regimen with portable apparatus (hereinafter called medication monitoring method). Referring to FIGS. 1 and 2 in which FIG. 1 schematically depicts a medication monitoring method in accordance with a first preferred embodiment of the invention and FIG. 2 depicts a perspective view of a blister package 2 shown in FIG. 1. The medication monitoring method is applicable to a portable apparatus 1 and a blister package 2.

The blister package 2 includes a plurality of blisters 21 and a unique identification code 22 disposed on the top surface of the blister package 2. The depicted unique identification code 22 is a combination of numbers and letters. In other embodiments, the unique identification code 22 is composed of numbers, letters, symbols, bar code, QR code, or a combination thereof in a non-limiting manner. Further, the unique identification code 22 is disposed on the blister package 2 by press printing, transfer printing, laser engraving, riveting or gluing other media onto the package in a non-limiting manner.

Notably, the unique identification code 22 is non-repeating among multiple blister packages and patients. Each unique identification code 22 is tied to a single blister package and belongs to a single patient's identity stored in a database. In other embodiments with multiple blister packages 2, each package would have a unique identification code 22. The portable apparatus 1 employed by the invention can distinguish the correct blister packages 2 belonging the correct patient using each package's unique identification code 22.

Specifically, this invention applies to blister package 2 that is factory-sealed by the original manufacturer, whereof the blister package 2 is not a retail pillbox. Hence a pharmacist does not have to remove medications out of the blister package 2 and redistribute them into a pillbox having a special shape, color, or functionality. As the result, contamination of the medication in the blister package 2 can be substantially avoided.

Figure 3:
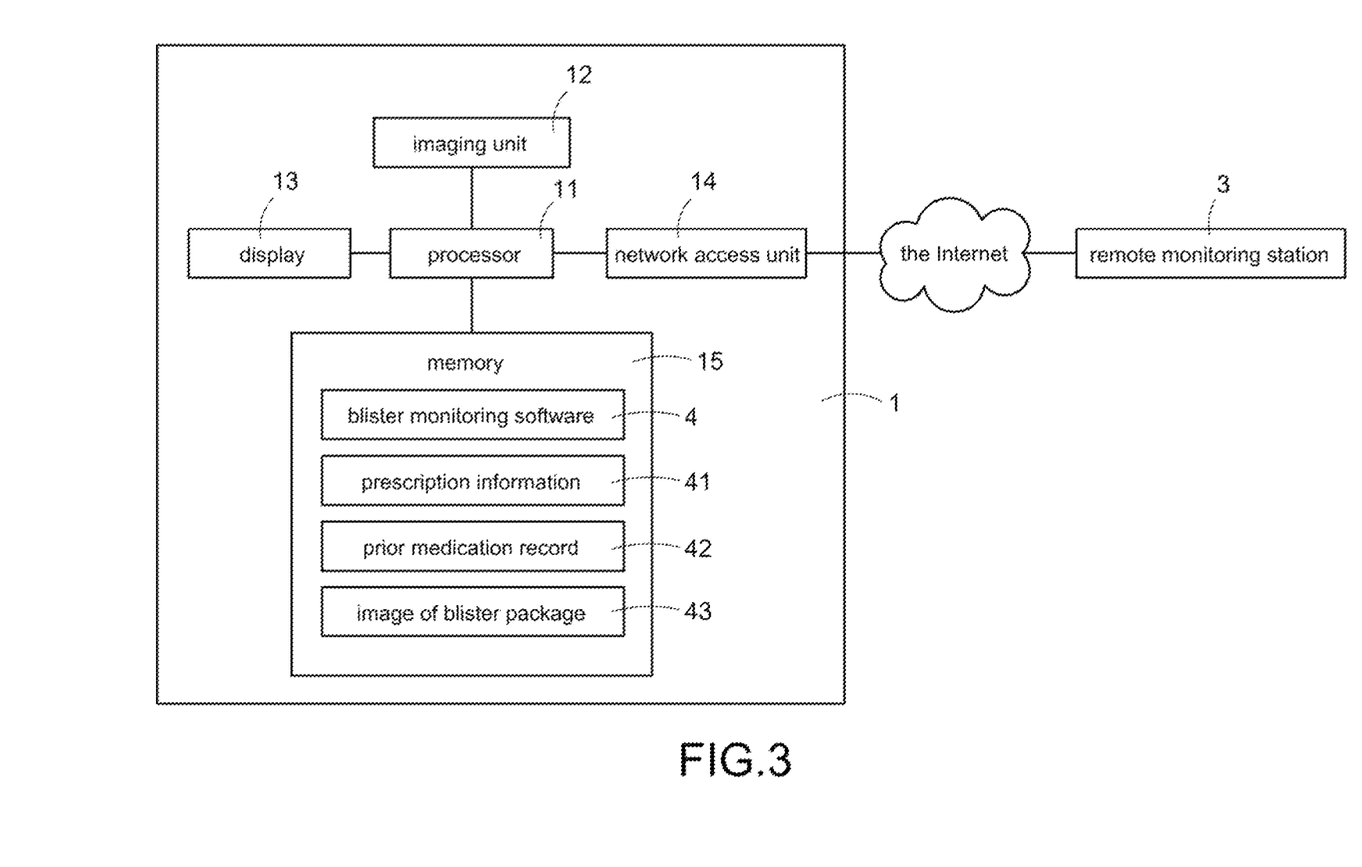
FIG. 3 depicts a block diagram of a portable apparatus in accordance with an embodiment of the invention.

The portable apparatus 1 includes blister monitoring software depicted in FIG. 3. Patient uses portable apparatus 1 to take an image of the blister package 2, and the blister monitoring software 4 analyzes the image to determine whether blister package 2's unique identification code 22 matches with patient identity and sends the quantity of the remaining tablets or capsules inside blister package 2 to a remote monitoring station 3. Doctors or nurses at the remote monitoring station 3 can thus track patient's medication regimen in real time.

FIG. 3 depicts a block diagram of the portable apparatus 1 of the first preferred embodiment of the invention. The portable apparatus 1 includes a processor 11, and an imaging unit 12, a display 13, a network access unit 14, and memory 15 all electronically connected to the processor 11.

The blister monitoring software 4 is stored in the memory 15. For performing medication monitoring method of the invention, a patient may operate the portable apparatus 1 to activate the processor 11 to turn on blister monitoring software 4. And in turn, the blister monitoring software 4 instructs portable apparatus 1 to activate imaging unit 12 to capture an image of blister package 2 and produce an image of the blister package 43. The image of the blister package 43 is stored in the memory 15. The processor 11 performs image analysis on the image of the blister package 43. Portable apparatus 1 then displays relevant prescription information, instructions, and processed image results to the patient via display 13. The portable apparatus 1 can access the Internet via network access unit 14 and relay relevant patient information to the remote monitoring station 3 where doctors and nurse can track a patient progress in real time.

As disclosed above, the invention can be implemented by simply using the portable apparatus 1 and running the blister monitoring software 4 installed in the portable apparatus 1. The portable apparatus 1 is lightweight and compact and can be easily held in the hand or fitted into the clothing pocket of a patient, making the invention highly convenient and mobile.

In one embodiment of medication monitoring method, the portable apparatus 1 can store prescription information 41 of the patient in a database inside memory 15. The prescription information 41 includes at least the prescribed medication time, patient's identity, and unique identification code 22 of the blister package 2 belonging to the patient, appearance of the blister package 2 and appearance of medication inside the package, dosage, and protocols of medication intake in a non-limiting manner.

Abovementioned blister monitoring software 4 activates the portable apparatus 1 on the prescribed medication time specified by the prescription information 41 to send and alert to patient to login blister monitoring software 4 with credentials or biometric features. And in turn, relevant prescription information 41 is shown to the patient.

Prior to taking medication, the blister monitoring software 4 instructs the patient with instructions shown on display 13 of the portable apparatus 1 to place the blister package 2 on any flat surface with the flat side of the blister package 2 facing down and the protruding side of the blister package 2 facing up. Imaging unit 12 of portable apparatus 1 then captures an image of the blister package 2, and blister monitoring software 4 then verifies the unique identification code 22 on blister package 2 with the patient's identity. If the verification fails, blister monitoring software 4 shows an alert for the patient with the expected package appearance and identification code via display 13.

After taking the medication, the patient uses imaging unit 12 of the portable apparatus 1 to capture another image of the blister package 2. Blister monitoring software 4 then analyzes the image for quantity of the remaining tablets or capsules inside blister package 2 and records the time of taking medication. Notably, blister monitoring software 4 also checks the remaining number of tablets or capsules inside blister package 2 with prescription information 41 to determine if the patient had taken too many or too few medications. In the case of under dose, display 13 of the portable apparatus 1 shows the correct dosage to the patient. In the case of overdose, portable apparatus 1 sends an alert to the remote monitoring station 3 via the Internet and doctors and nurses at the remote monitoring station 3 can take immediate actions.

Figure 4:
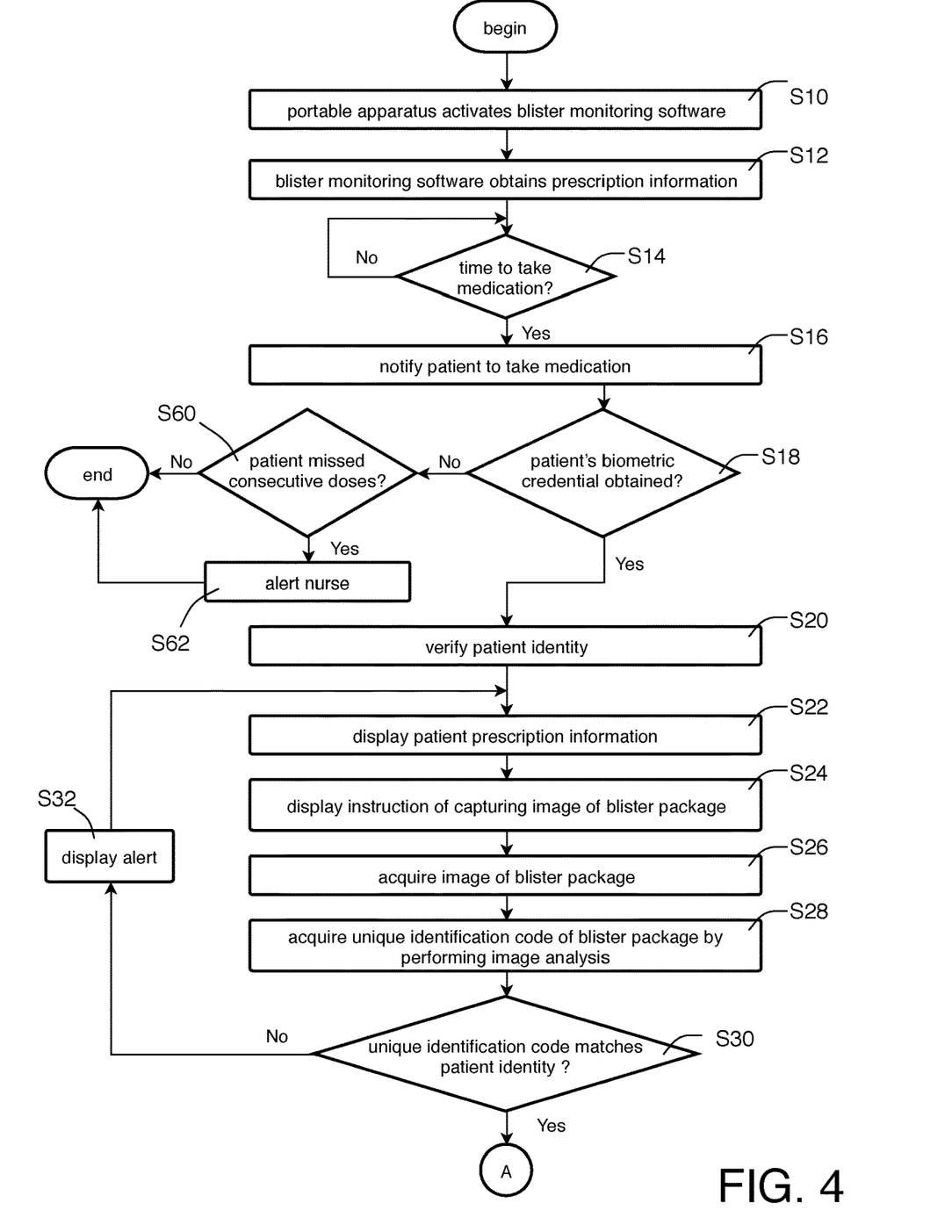
FIG. 4 depicts a flow chart of a medication monitoring method in accordance with an embodiment of the invention.
Figure 5:
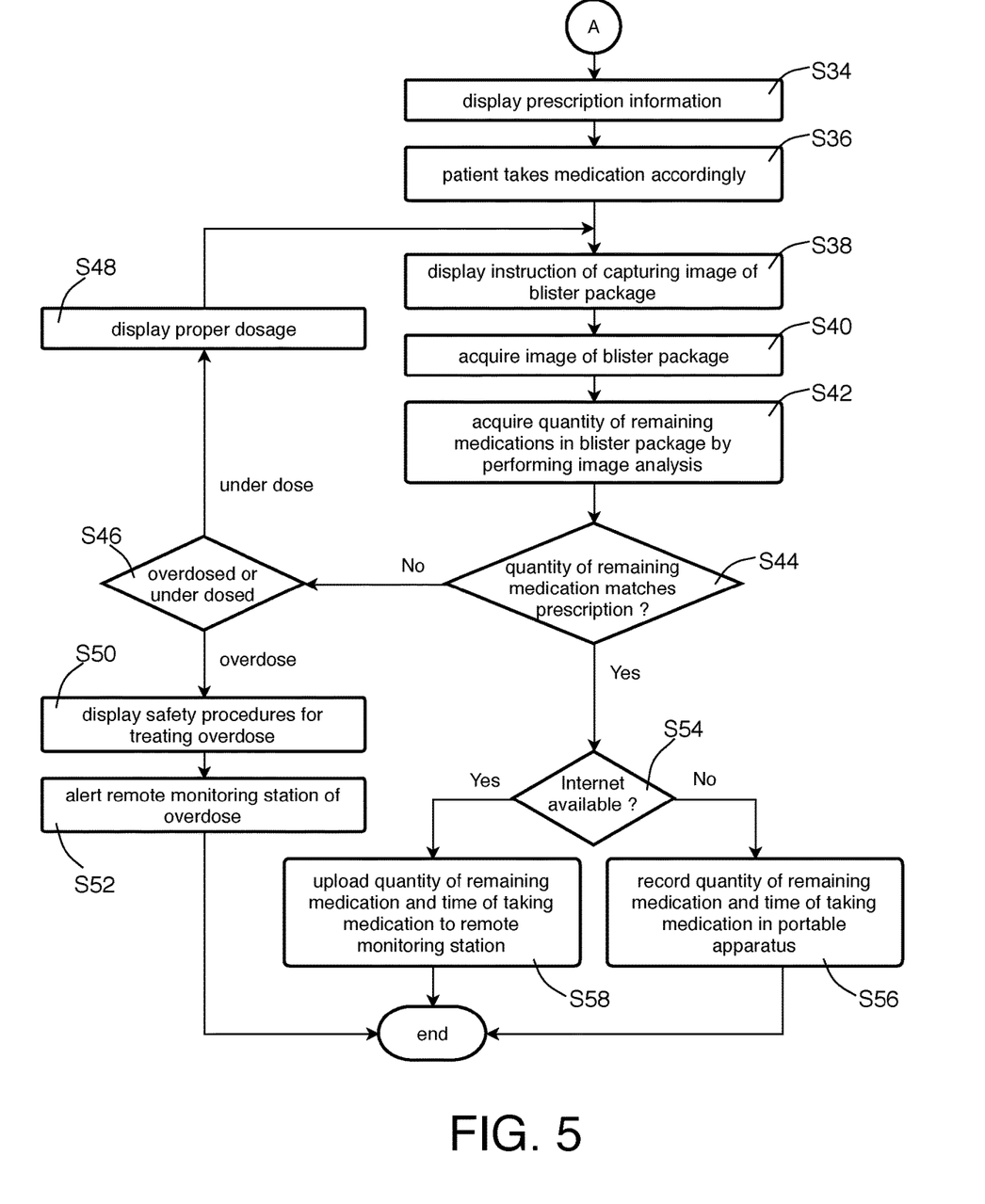
FIG. 5 continues the flow chart of FIG. 4. of a medication monitoring method in accordance with an embodiment of the invention.

FIG. 4 depicts a flow chart of a medication monitoring method in accordance with an embodiment of the invention and FIG. 5 continues the flow chart for further disclosure of the method. The medication monitoring method starts with a patient turning on portable apparatus 1 and activates blister monitoring software 4 (step S10). Next, blister monitoring software 4 obtains prescription information 41 (step S12). Blister monitoring software 4 may additionally obtain prior medication record 42 of the patient in a non-limiting manner.

Specifically, prescription information 41 and prior medication record 42 can be entered by the patient or a physician directly into blister monitoring software 4, or be retrieved from records stored in local memory 15 of the portable apparatus 1. In another embodiment, after the patient has logged in, the blister monitoring software 4 can retrieve prescription information 41 and prior medication record 42 from a remote server via internet (not depicted in flow chart) in a non-limiting manner.

Prescription information 41 contains the prescribed medication time set by the prescription for one or multiple medications. After step S12, blister monitoring software 4 retrieves the prescribed medication time from prescription information 41 and determines if any of the prescribed medication time is due now (step S14). On the prescribed medication time, the blister monitoring software 4 notifies the patient to take medication via portable apparatus 1 (step S16).

In the preferred embodiment, multiple patient prescriptions for different patients can be stored in blister monitoring software 4 or local memory 15. In the above steps (S10~S16), the blister monitoring software 4 reads multiple prescription information 41 simultaneously to obtain multiple prescribed medication time. On the prescribed medication time set by any one prescription, blister monitoring software 4 issues a notification via portable apparatus 1 for the corresponding patient to take medication. Thus, the medication monitoring method can assist multiple patients concurrently using only one portable apparatus 1, making the process efficient and convenient.

After the patient receives the notification from step S16, the patient is required to enter biometric credentials such as fingerprints or facial features to blister monitoring software 4 via portable apparatus 1 (S18). Next, step S20 verifies the patient credential to login patient into blister monitoring software 4.

Notably, if the patient does not provide any login credential in step S18 after a period of time, the patient is deemed to have missed his or her medication, and step S60 determines if the patient has already missed a number of previous medications (e.g., missed 2 previous medications). In the case of consecutively missing medication, blister monitoring software 4 alerts a remote monitoring nurse to contact the patient and resolve the cause of missing doses (step S62). For example, a nurse can contact the patient via telephone to determine if the patient has lost his or her medication packages and arrange an appointment to administer new packages, thus avoiding delay in clinical trial.

After the patient credential has been verified in step S20, blister monitoring software 4 displays the patient's prescription information 41 on display 13 of the portable apparatus 1 (step S22). The patient can thus confirm his or her identity as the intended medication recipient and be reminded of his or her prior medication records 42 as well as relevant prescription information 41 such as the appearance of blister package and medication. Blister monitoring software 4 then utilizes display 13 to show the instructions of capturing an image of the blister package 43 using imaging unit 12 (step S24).

Abovementioned step S22 and S24 are intended to provide relevant prescription information and instructions for guiding the patient to capture an image of blister package 43. In other embodiments, steps S22 and S24 can be optional.

After step S24, step S26 instructs the patient to place the blister package 2 on a flat surface with the package's flat side facing down and the protruding side facing up, and operate portable apparatus 1 to capture an image of the blister package 43. After obtaining the image of the blister package 43, blister monitoring software 4 runs image recognition analysis on the image to extract the blister package's unique identification code 22 (Step S28).

Blister monitoring software 4 then compares patient identity with the unique identification code 22 to determine if the patient has acquired the correct blister package in step S30. If the wrong blister package is found, an alert is shown on display 13 in step S32 and the process returns to step S22 showing the appearance of the proper blister package, and instructs the patient to capture another image of the blister package 43 of the correct package.

Specifically, when blister monitoring software 4 finds the correct identification code 22 matching the patient, step S34 shows relevant prescription information 41 such as how to swallow or sublingual diffuse the medication under the tongue via portable apparatus 1's display 13. The patient can then take the medication from blister package 2 accordingly (step S36), and uses blister monitoring software 4 to record the time of taking medication and the quantity of remaining tablets or capsules inside blister package 2.

After the patient has taken the medication, blister monitoring software 4 uses portable apparatus 1's display 13 to show the instruction of capturing another image of blister package 43 (step S38), and the patient can image the blister package 2 accordingly (step S40).

Specifically, after the patient has taken the medication, the quantity of the tablets or capsules inside blister package 2 is decreased, and the decreased number of tablets or capsules should equal to the prescribed dosage per medication session specified by prescription information 41. Under normal circumstances, blister monitoring software 4 should acquire a new quantity of remaining tablets or capsules from the image of the blister package 43 in step S40 that is different from the quantity of remaining tablets or capsules acquired in step S26 or the quantity of remaining tablets or capsules from previous medication session stored in prior medication record 42.

After step S40, blister monitoring software 4 conducts image analysis on image of blister package 43 to acquire quantity of remaining tablets or capsules in blister package 2 (step S42). The quantity of remaining tablets or capsules and the time of taking medication (taken as the present time of portable apparatus 1) are recorded inside memory 15 of portable apparatus 1, in a remote database, or in the remote monitoring station 3 in a non-limiting manner.

After obtaining the quantity of remaining tablets or capsules in blister package 2, blister monitoring software 4 compares the quantity of remaining tablets or capsules to the dosage requirement in prescription information 41, and determines if the right amount of medication remains (step S44). If the quantity of remaining tablets or capsules is incorrect, step S46 then determines if the patient is overdosed or under dosed.

In another embodiment of step S44, blister monitoring software 4 can verify the quantity of remaining tablets or capsules against prior medication records 42 and prescription information 41 to determine if the proper dosage has been taken.

Subsequently, if the blister monitoring software 4 determines that the patient is under dosed in step S46 (e.g., the quantity of remaining tablets or capsules was previously ten and the quantity of remaining tablets or capsules after the current session is nine, but the prescribed dosage per medication session specified by prescription information 41 is three per session), then blister monitoring software 4 utilizes display 13 of the portable apparatus 1 to present the correct medication dosage per session to the patient in step S48. The process then returns to step S38 and waits for patient to administer the correct dosage and capture another image of the blister package 43. Thus, the medication monitoring method can promptly alert the patient of under dose and ensures the proper dosage is taken.

Subsequently, if the blister monitoring software 4 determines that patient is overdosed in step S46 (e.g., the quantity of remaining tablets or capsules was previously ten and the quantity of remaining tablets or capsules after the current session is five, but the prescribed dosage per medication session specified by prescription information 41 is three per session), then blister monitoring software 4 utilizes display 13 of the portable apparatus 1 to display safety procedures for treating overdose (step S50), such as ingesting large amount of water and contacting emergency personnel, and simultaneously alerts doctors and nurse at remote monitoring station 3 (step S52). Thus, the medication monitoring method can promptly alert emergency personnel or doctors and nurses of overdose and ensures patient safety.

If the blister monitoring software 4 determines that the quantity of remaining tablets or capsules is correct in step S44 and the patient has taken the correct dosage, it then checks whether portable apparatus 1 is connected to the Internet (step S54).

If no Internet connection is available, blister monitoring software 4 records the quantity of remaining tablets or capsules and the time of taking medication inside portable apparatus 1 and updates medication record 42 accordingly (step S56). If Internet connection is available, blister monitoring software 4 uploads the quantity of remaining tablets or capsules and the time of taking medication to remote monitoring station 3 so the patient's progress can be remotely tracked by doctors and nurses (step S58).

Notably, the patient can continue to use this medication monitoring method without Internet connection, and blister monitoring software 4 will synchronize patient's medication record with remote monitoring station 3 when the portable apparatus 1 regains Internet connection in step S58.

The medication monitoring method disclosed above uses blister monitoring software 4's image recognition capability to determine if the image of blister package 43 matches patient credential. However, the patient can capture an image of blister package 43 against a visually noisy background, making image recognition process difficult and time consuming. Further, portable apparatus 1 has increasingly high resolution imaging unit 13 yet usually do not have high power processor 11 compare to a desktop computer or a server, and the monitoring method must continue to work when there is no Internet connection for offloading computation to a remote server. Thus, a practical and efficient method of locating the blister package in the image of blister package 43 using portable apparatus 1 must be devised.

Figure 6:
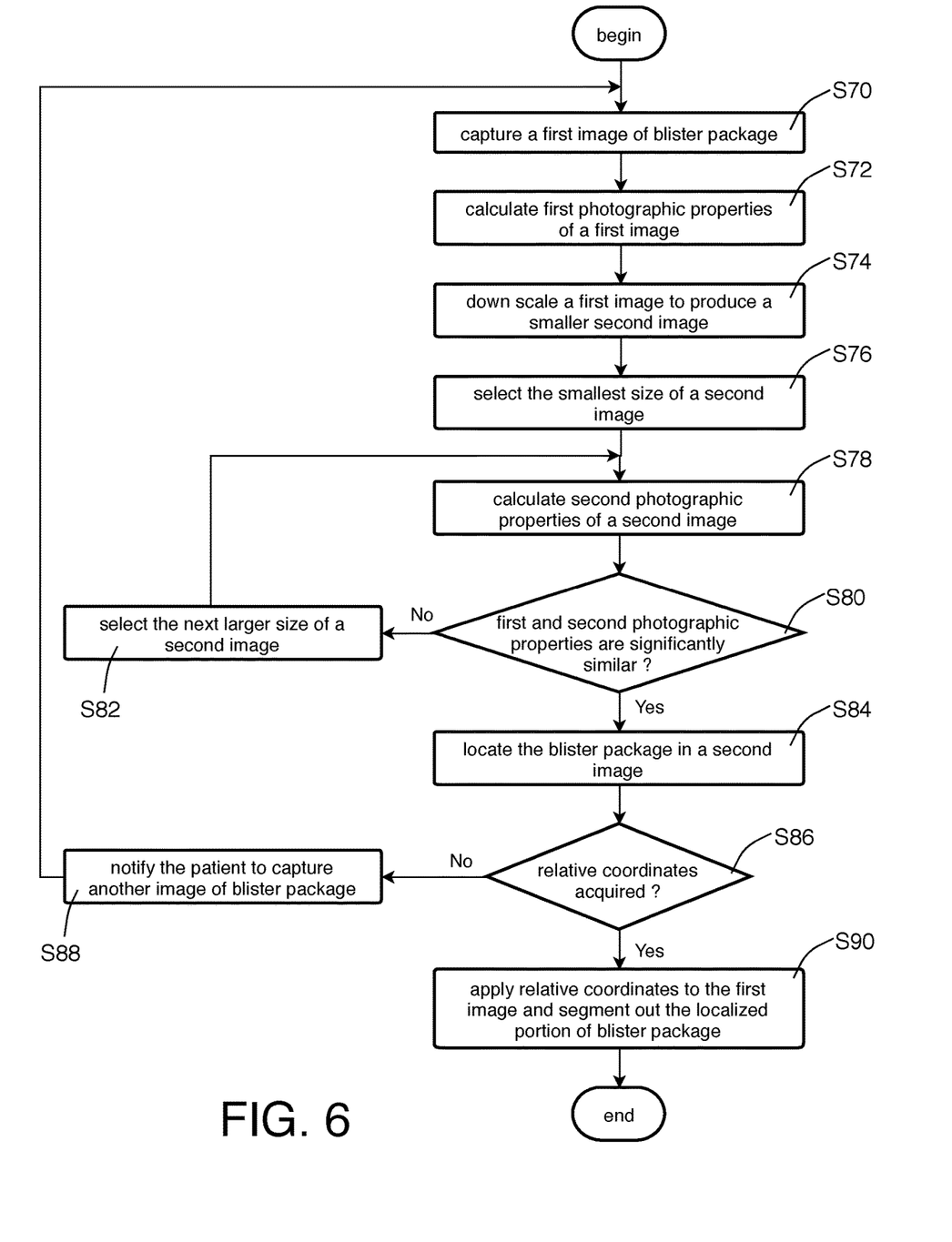
FIG. 6 depicts a flowchart of a rapid blister package localizing method in accordance with an embodiment of the invention.

FIG. 6 depicts a flowchart of a rapid blister package localizing method in accordance with an embodiment of the invention. The steps depicted in FIG. 6 further disclose abovementioned steps S26 and S40 in greater detail. The steps in FIG. 6 describe how the present invention scales down the image of blister package 43, filters out unwanted portion of image 43, and rapidly segment out a localized image of blister package 2 for further image analysis in steps S28 and S42 while reducing processing time on processor 11.

Referring to FIG. 6, the localizing method begins with imaging unit 12 capturing a first image of blister package 2 (i.e., the image of blister package 43) against an arbitrary background (step S70). Then, blister monitoring software 4 calculates a set of first photographic properties of the first image of blister package 2 (step S72). Said first photographic properties are computationally lightweight to obtain and compatible with different image scales. In a first embodiment of rapid blister package localizing process, said first photographic properties of the first image of blister package 2 include but are not limited to histograms of pixel's red intensity, histograms of pixel's green intensity, histograms of pixel's blue intensity and histograms of pixel chromaticity, and histograms of length of linear edges and radius of circular edges, where the edges are constructed from pixels with high variation in intensity.

After step S72, blister monitoring software 4 applies down-scaling of the first image of blister package 2 to produce a smaller second image (step S74). In a first embodiment of rapid blister package localizing process, blister monitoring software 4 starts the down-scaling of the first image with the smallest scale, such as 10% of the original size, then gradually increase to larger scale such as 20%, 30%, 40% etc. of the original size (step S76). Blister monitoring software 4 then calculates a set of second photographic properties of the smaller second image (step S78). Said second photographic properties obtained in step S78 are calculated using the same algorithm as the first photographic properties obtained in step S72. Said second photographic properties of the smaller second image of blister package 2 include but are not limited to histograms of pixel's red intensity, histograms of pixel's green intensity, histograms of pixel's blue intensity and histograms of pixel chromaticity and histograms of length of linear edges and radius of circular edges.

After step S78, blister monitoring software 4 compares the first photographic properties against the second photographic properties to determine if they are similar, such that the smaller second image retains sufficient features of first image such as the edges of different objects in the image and the visual boundaries of individual blisters (step S80). If the properties are closely matched (e.g., 90% similar), the smaller second image is deemed to have enough details for further processing by blister monitoring software 4.

If the first photographic properties and the second photographic properties are dissimilar, then blister monitoring software 4 produces a new image with a larger scale such as 20% of the original image size (step S82), and returns to step S78 to recalculate the second photographic properties of the new, larger-scaled second image. The process of resizing first image, calculating second photographic properties, comparing first and second photographic properties from step S78 to S82 can repeat until the details of smaller second image are deemed sufficiently similar to the first image and permits further processing.

If the first photographic properties and the second photographic properties are significantly similar, blister monitoring software 4 uses multiple approaches to determine the relative coordinates of the blister package 2 in the smaller second image (step S84).

Blister monitoring software 4 then determines if blister package 2 has been successfully located in step S86. If the details of smaller second image are deemed sufficiently similar to the first image, but blister monitoring software 4 is still unable to locate blister package 2, then the first image is possibly too blurry, too dim or contains no blister package 2 at all. Thus, blister monitoring software 4 notifies the patient to capture another image of blister package 2 via display 13 of portable apparatus 1 (step S88). The process then returns to S70 with the patient operating imaging unit 12 to capture another first image of blister package 2.

In another embodiment of a rapid blister package localizing method, the imaging unit 12 is running in a continuously recording mode, and step S70 to S88 is a software loop that continuously checks for blister package in a first image, and step S76 to S82 is a nested software loop that continuously checks the properties of a smaller second image. The process of rapid blister package localizing method thus operates in a real-time scanning mode and the patient simply aims portable apparatus 1 at blister package 2 and the process will automatically complete itself in step S90.

If blister monitoring software 4 successfully locates blister package 2 in the smaller second image and obtains the relative coordinates of blister package 2, the relative coordinates are then applied to the first image to segment out a localized image of blister package 2 (step S90).

Specifically, abovementioned step S84 can include, but not limit to, the following approaches to locate blister package 2.

In a first embodiment of rapid blister package localizing method of blister package 2, blister monitoring software 4 can search for the distinctive aluminum surface of blister package 2, since aluminum lidding are widely used in heat-sealed blister packages. This method only searches for one feature of the blister package 2 and is computationally lightweight.

In a second embodiment of rapid blister package localizing method of blister package 2, blister monitoring software 4 can search for common geometric shapes of blisters, tablets and capsules, such as circle, oval, rectangle, circular rectangle, triangle, rhombus, pentagon, hexagon and octagon, as well as other machine-learned features such as plastic wrinkles and reflections, repeating patterns of rows and columns, and then determine the location of blister package 2 by statistically clustering the distribution of these features. This method is slower than detecting aluminum surface because numerous geometric filters need to be applied.

In a third embodiment of rapid blister package localizing method of blister package 2, blister monitoring software 4 can feed the entire smaller second image into an artificial neural network and output the relative coordinates of blister package 2 directly. This method can adjust between detection accuracy and detection speed by varying the number of layers in the network. More layers will yield higher detection accuracy at cost of slower detection speed.

Abovementioned machine learning and artificial neural network are common knowledge in image processing, and their details are thus omitted.

Another distinct feature of medication monitoring method is to use blister monitoring software 4 to analyze the localized image of blister package 2 produced in step S90 to determine if the quantity of remaining tablets or capsules in blister package 2 complies with prescription information 41. Knowing the quantity of remaining tablets or capsules allows tracking of patient's dosage in each medication session, reduces risk of overdose and under dose, and increases patient compliance. Therefore, this invention discloses a rapid medication counting method that can quickly and accurately determine the quantity of remaining tablets or capsules inside blister package 2.

Figure 7:
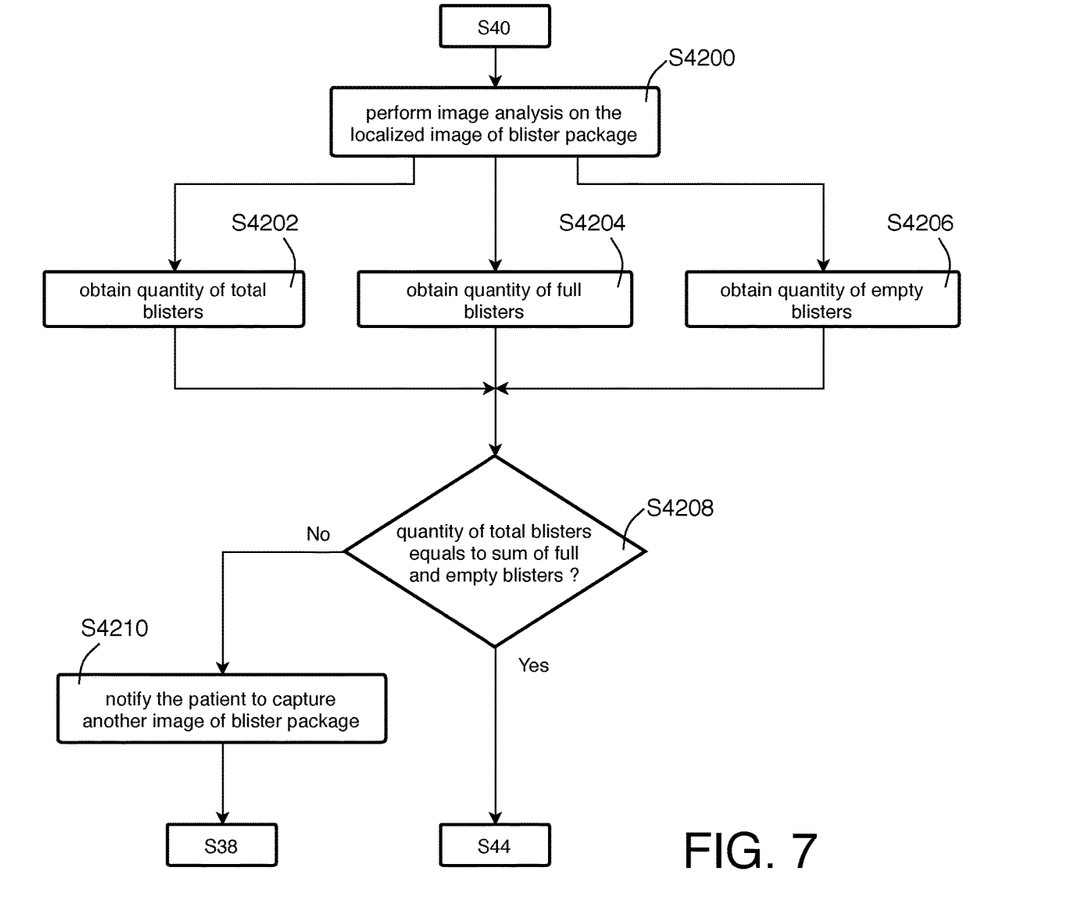
FIG. 7 depicts a flowchart of a rapid medication counting method in accordance with an embodiment of the invention.

FIG. 7 depicts a flowchart of a rapid medication counting method in accordance with an embodiment of the invention. The steps depicted in FIG. 7 further disclose abovementioned step S42 in greater detail. The steps in FIG. 7 describe how the rapid medication counting method compares the sum of full and empty blisters against the total quantity of blisters.

After blister monitoring software 4 obtains image of the blister package 43 in step S40 and segments localized image of blister package 2 in step S90, it then performs a rapid medication counting method on the localized image of blister package 2 (step S4200) and obtains quantity of total blisters 21 (step S4202), quantity of full blisters 211 (step S4204) and quantity of empty blisters 212 (step S4206).

Figure 8:
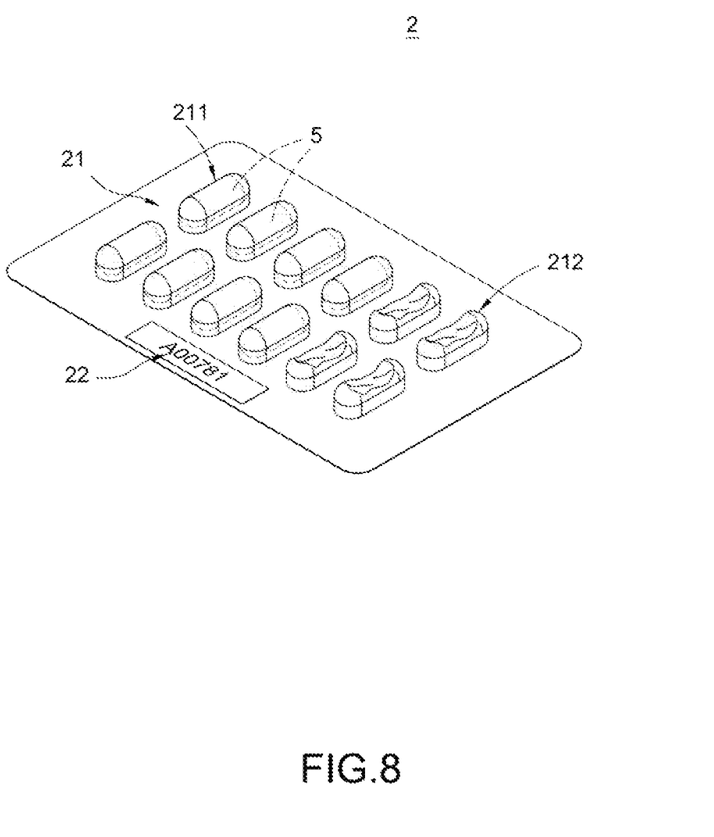
FIG. 8 depicts a perspective view of a blister package according to a second preferred embodiment of the invention.

Referring to FIG. 8 which depicts a perspective view of a blister package according to a second preferred embodiment of the invention, a blister package 2 having multiple and immutable number of blisters, thereof the number of blisters is the abovementioned quantity of total blisters 21. If the medication 5 is still sealed inside blister, thereof the number of blisters containing medication is the abovementioned quantity of full blisters 211. If the medication 5 has been taken out of blister and blister seal is broken, thereof the number of blisters containing no medication is the abovementioned quantity of empty blisters 212.

Returning to FIG. 7. After obtaining quantity of total blisters 21, quantity of full blisters 211 and quantity of empty blisters 212, blister monitoring software 4 compares the quantity of total blisters 21 against the sum of quantity of full blisters 211 and quantity of empty blisters 212 (step S4208). Step S4208 ensures the result of a rapid medication counting method are correct and not influenced by possible deformations or stains on the blister package 2, or by possible blurriness or distortions on the localized image of blister package 2.

If blister monitoring software 4 determines quantity of total blisters 21 matches sum of quantity of full blisters 211 and quantity of empty blisters 212, the process then continues to step S44 to determine if the quantity of remaining tablets or capsules complies with prescription information 41. If the quantities of remaining tablets or capsules of the blisters do not match, then the rapid medication counting method fails and an alert is sent to display 13 to instruct the patient to recapture the image of blister package 43 (step S4210). The process then returns to S38 and waits for new image of blister package 43.

Specifically, step S4200 can include, but not limit to, the following rapid medication counting methods for acquiring the quantities 21, 211 and 212 of total, full and empty blisters respectively.

The first embodiment of a rapid medication counting method scans the localized image of blister package for common blister geometry such as circle, oval, rectangle, circular rectangle, triangle, rhombus, pentagon, hexagon, octagon, as well as machine learned features such as plastic wrinkles and reflections, and then statistically clusters these features to determine the total number of blisters.

The second embodiment of a rapid medication counting method scans the localized image of blister package for small patches of color as tablets and capsules are usually composed of only one or two colors. Specifically, an area of uniform colors can be seen as one full blister.

The third embodiment of a rapid medication counting method scans the localized image of blister package for textures of heat-sealed aluminum lidding surrounding each blister and inversely selects these areas to isolate the full blisters. Since tablets or capsules block out aluminum lidding with a smooth visual boundary, an area with smooth boundary and without aluminum lidding can be seen as one full blister.

The fourth embodiment of a rapid medication counting method scans the localized image of blister package for lines and ridges of plastic wrinkles and broken seals, and clusters these features into areas of empty blisters.

The fifth embodiment of a rapid medication counting method scans the localized image of blister package for machine learned features of empty blisters, and clusters these features into areas of empty blisters. These features are automatically learned by machine and not specified by human intelligence.

The sixth embodiment of a rapid medication counting method feeds the entire localized image of blister package into an artificial neural network and outputs quantity of total blisters 21, quantity of full blisters 211 and quantity of empty blisters 212 directly.

The method of monitoring medication regimen with portable apparatus can remind the patients of their medication, and utilizes image recognition to prevent the patient from taking the wrong medication, as well as tracking the patient's medical regimen in real time, thus greatly increases patient compliance, convenience of recording and carrying mobility. In addition, the invention can be applied to factory-sealed blister packages so that personnel cost for hospital and risk of medication contamination are greatly reduced.

The above description is only a preferred embodiment of the present invention, and is not intended to limit the scope of the present invention. Therefore, modifications obvious to those skilled in the art should be included in the scope of the present invention.

What is claimed is:

1. A medication monitoring method for collecting medication usage data applied for a portable apparatus installed with a blister monitoring software, and a blister package having a unique identification code disposed thereon and having a plurality of blisters containing tablets or capsules, the medication monitoring method comprising following steps of:
    a) using said blister monitoring software to display a notification via said portable apparatus at a prescribed medication time, wherein the blister monitoring software stores a prescription information, the prescription information comprises the patient's identity, the unique identification code of the blister package belonging to the patient's identity, the prescribed medication time, the prescribed dosage per medication session, an appearance of the blister package, an appearance of prescribed medication, and the protocols of medication intake, and step a) comprises:
        automatically reading the prescription information for retrieving the prescribed medication time when said blister monitoring software is activated; and
        displaying the notification via said portable apparatus at the prescribed medication time;
    b) obtaining a biometric credential of a patient using said portable apparatus for logging into said blister monitoring software and verifying the patient's identity;
    c) capturing an image of said blister package using said portable apparatus;
    d) analyzing the image of said blister package to obtain said unique identification code on the blister package;
    e) comparing the patient's identity to said unique identification code to determine if said blister package belongs to the patient;
    f) displaying an alert via said portable apparatus if said blister package is determined not belonging to the patient; and
    g) recording a quantity of remaining tablets or capsules inside said blister package and patient's time of taking medication if said blister package is determined as belonging to the patient, comprising:
        g1) displaying protocols of medication intake from patient's corresponding prescription information on the display of said portable apparatus when said unique identification code is determined matching the patient's identity;
        g2) displaying instructions of capturing an image of said blister package after the patient has taken medication;
        g3) capturing the image of said blister package using said portable apparatus;
        g4) obtaining the quantity of the remaining tablets or capsules inside said blister package using image recognition methods on the image of said blister package; and
        g5) recording current device time of said portable apparatus as the patient's time of taking medication.

2. The medication monitoring method in claim 1, wherein said unique identification code is disposed on a surface of a protruding side of said blister package and is composed of numbers, letters, symbols, barcode, QR code or combinations thereof, and wherein said biometric credential is one of patient's fingerprints or facial features.

3. The medication monitoring method in claim 1, wherein said blister monitoring software is configured to store plurality of the prescription information; and
    wherein the step a) comprises:

automatically reading all the prescription information; and displaying the notification when any of the prescribed medication times of the plurality of prescription information is due.

4. The medication monitoring method in claim 1, further comprising following steps after the step a):

a1) determining if the patient has missed multiple medications consecutively after said portable apparatus fails to obtain the patient's credential; and a2) alerting a nurse at a remote monitoring station to contact the patient and resolve the cause of consecutively missing multiple medications.

5. The medication monitoring method in claim 1, further comprising following steps before the step c):

displaying the prescription information; and displaying instructions of capturing an image of said blister package.

6. The medication monitoring method in claim 1, wherein the step g4) comprises the steps of:

g41) analyzing the image of said blister package to obtain the quantity of remaining tablets or capsules inside said blister package;

g42) comparing the quantity of the remaining tablets or capsules inside said blister package to the prescription information and prior medication records to determine if a remaining quantity of tablets or capsules is correct;

g43) determining whether the patient is overdosed or under dosed when the remaining quantity of tablets or capsules is determined incorrect;

g44) displaying the prescribed dosage per medication session on said portable apparatus and returning to the step g2) when the patient is determined under dosed; and g45) displaying safety procedures on said portable apparatus and alerting nurses on a remote monitoring station when the patient is determined overdosed.

7. The medication monitoring method in claim 6, wherein the step g4) further comprises the steps of:

g46) determining whether the portable apparatus is connected to the Internet if the quantity of remaining tablets or capsules inside said blister package equals to the prescription information;

g47) recording the quantity of remaining tablets or capsules inside said blister package in the remote monitoring station when the Internet is available; and g48) recording the quantity of remaining tablets or capsules inside said blister package in said portable apparatus for updating the prior medication records.

8. The medication monitoring method in claim 6, wherein the step g41) further comprises the steps of:

g411) obtaining a quantity of total blisters of said blister package by analyzing the image of the said blister package;

g412) obtaining a quantity of full blisters of said blister package by analyzing the image of the said blister package;

g413) obtaining a quantity of empty blisters of said blister package by analyzing the image of the said blister package;

g414) determining if the quantity of total blisters equals to a sum of the quantity of full blisters plus the quantity of empty blisters;

g415) performing the step g42) when the quantity of total blisters equals to the sum of the quantity of full blisters plus the quantity of empty blisters; and g416) displaying instructions on said portable apparatus of recapturing the image of said blister package and returning to the step g3) when the quantity of total blisters is determined not equal to the sum of the quantity of full blisters plus the quantity of empty blisters.

9. The medication monitoring method in claim 1, wherein the step c) further comprises the steps of:

c1) capturing a first image of said blister package using said portable apparatus;

c2) calculating a plurality of first photographic properties of the first image of said blister package;

c3) reducing the first image of said blister package to multiple smaller sizes to produce a set of second images of said blister package;

c4) calculating a plurality of second photographic properties of one of the second images of said blister package;

c5) determining if the first photographic properties of the first image and the second photographic properties of the second image are significantly similar;

c6) selecting next second image with next image size in the step c3) of a larger dimension and returning to the steps c4) and the step c5) when the first photographic properties of the first image and the second photographic properties of the second image are significantly different;

c7) locating said blister package and obtaining its relative coordinate in the second image when the first photographic properties of the first image and the second photographic properties of the second image are significantly similar;

c8) displaying instructions on said portable apparatus of recapturing the first image of said blister package when the step c7) fails to locate said blister package; and c9) localizing and extracting portions of the first image corresponding to said blister package using the relative coordinates from the step c7) as the image of said blister package after said blister package has been successfully located.

10. The medication monitoring method in claim 9, wherein said plurality of first photographic properties of the first image of said blister package contains at least one histogram of pixel's red intensity, histogram of pixel's green intensity, histogram of pixel's blue intensity, histogram of pixel's chromaticity, histogram of linear edge's length, histogram of circular edge's radius, and wherein said plurality of second photographic properties of the second image of said blister package contains at least one histogram of pixel's red intensity, histogram of pixel's green intensity, histogram of pixel's blue intensity, histogram of pixel's chromaticity, histogram of linear edge's length, histogram of circular edge's radius.

* * * * *